United States Patent [19]
Steinberg et al.

[11] Patent Number: 5,888,486
[45] Date of Patent: Mar. 30, 1999

[54] ANTIPERSPIRANT COMPOSITIONS

[75] Inventors: David Steinberg, Plainsboro, N.J.; Anthony J. O'Lenick, Jr., Dacula, Ga.

[73] Assignees: Lambent Technologies Inc., Norcross, Ga.; Hansotech Inc., Woodbury, N.Y.

[21] Appl. No.: 979,718

[22] Filed: Nov. 28, 1997

[51] Int. Cl.⁶ .................. A61K 7/32; A61K 7/00
[52] U.S. Cl. .................. 424/65; 424/66; 424/67; 424/68; 424/400; 424/401
[58] Field of Search .................. 424/65, 66, 67, 424/68, 400, 401

[56] References Cited

U.S. PATENT DOCUMENTS 4,229,432  10/1980  Geria .......................... 424/68
5,635,166   6/1997  Galleguillos ................. 424/66

*Primary Examiner*—Shelley A. Dodson

[57] ABSTRACT

The present invention is directed to antiperspirant compositions comprising an antiperspirant compound, like an astringent salt; a cyclomethicone, a silicone polymer wax derived from beeswax and a fatty alcohol. The antiperspirant compositions are viscous compositions that are highly stable and essentially non-whitening and non-staining to skin and clothing after topical application. These desirable properties are attained by the inclusion of the specific silicone compound derived from beeswax.

10 Claims, No Drawings

ANTIPERSPIRANT COMPOSITIONS

BACKGROUND OF THE INVENTION

Antiperspirant compositions are well known in the personal care art. Ideally antiperspirant compositions are stable compositions that effectively deliver the antiperspirant compound to the skin. In addition, the composition should not leave a visually observable white residue that transfers to the skin or clothing. Deposition of a white residue is esthetically unappealing to the consumer.

Antiperspirant compositions are available in a variety of forms such as aerosol, suspensions, pump, sprays, roll on, powders emulsions, suspensions and solid gels. Antiperspirant compositions additionally have been prepared as either oil in water emulsions or water in oil emulsions. Therefore, antiperspirant compositions of any form typically have a milky or opaque appearance and are manufactured by complex methods. These emulsions contain several types of materials that are insoluble in each other. They include organic oils, silicone compounds, cyclomethicone and water. It is highly desirable to have an additive to place into the composition that will cause all of these various phases that are immicible in each other to form one uniform emulsion, which does not separate. We have surprisingly found a material that contributes this stability and provides outstanding slip to the composition. The inclusion of the compounds into an antiperspirant composition results in an unexpected highly uniform film when applied to the skin. Consequently, a superior heretofore-unattainable antiperspirant results. These properties are highly prized by consumer.

Non-emulsified antiperspirant compositions also are known in the art. However, non-emulsified compositions often require shaking prior to each use in order to re-disperse the insoluble antiperspirant compound that has separated from the compositions. Non-emulsifier antiperspirant compositions that do not require shaking prior to use, are typically pastes or creams that require a high percentage of thickening agents like organo-clay. The presence of organo-clay in the composition is a principal source of the whitening and staining of skin and clothing.

Investigators have searched for antiperspirant compositions that are highly uniform, do not contribute residue to skin or clothes, go on to the skin smoothly and do not separate with time. The inclusion of a specific class of silicone compounds derived from beeswax addresses all of these desired properties.

A roll-on antiperspirant is difficult to formulate and manufacture because the composition requires a sufficient viscosity to adhere to the skin, resist dripping off or running down the skin, and yet is not tacky or sticky. A gel antiperspirant composition is difficult to formulate and manufacture because the composition requires sufficient firmness to withstand rubbing across the skin to deliver a sufficient amount of antiperspirant compound to the skin. Additional formulation parameters include viscosity control lack of syneresis and tackiness.

However, providing a commercially acceptable antiperspirant composition requires overcoming several formulations and manufacturing problems. Antiperspirant compositions, especially in the roll-on or gel form are particularly favored by consumers because such products are esthetically appealing and project the appearance of product purity safety, good performance and being non-whitening. However, due to formulation instability and the difficult manufacture of transparent antiperspirant compositions are not now available to the consumer.

Solid antiperspirant compositions may be divided into three main classes, (a) compressed powder sticks (b) gelled sticks and (c) wax sticks. Each of the three classes has advantages and each also has particular disadvantages. Compressed powder sticks for example, are frequently brittle and hard and leave a cosmetically unacceptable powdery residue after application. Frequently, wax-based products are cosmetically unacceptable because of such factors as hardness, greasiness and tackiness. The opacity of wax sticks and the visually observable white residue that remains after application is also esthetically unacceptable.

Gel type solid antiperspirant compositions have several advantages over both compressed powder sticks and wax sticks. For example, the gel antiperspirant compositions leave fewer residues or dust on the skin. The gel antiperspirant compositions glide more easily over the skin surface resulting in easy and comfortable application of the composition However, preparation of antiperspirant compositions in the form of a stable gel is difficult. For example, a critical ingredient in the gel antiperspirant composition is the gelling agent. Many prior gel antiperspirant compositions comprise hydroalcoholic solutions including a gelling agent such as sodium stearate to form the gel. However, common gelling agent cannot be used in the presence of acidic antiperspirant compounds because of an interaction between the gelling agent which is alkaline and the antiperspirant compound that is acidic.

OBJECT OF THE INVENTION

It is the object of the present invention to provide cosmetically elegant antiperspirant compositions that offer the consumer a smooth easily spread stick that is free of whitening and crystallization.

SUMMARY OF THE INVENTION

The antiperspirant compositions of the current invention comprise:

1. An antiperspirant active selected from the group consisting of aluminum chlorohydride, aluminum dichlorohydrate, aluminum sesquichlorohydrate, Aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesqichlorohydrex polyethylene glycol complex, aluminum zirconium trichlorohydrate, aluminum zirconium tetrachlorohydrate, aluminum zirconium pentachlorohydrate, aluminum zirconium octachlorohydrate, aluminum zirconium trichlorohydrex glycerin complex, aluminum zirconium pentachlorohydrex glycerin complex, aluminum zirconium octachlorohydrex glycerin complex, aluminum chloride and aluminum sulfate buffered. Antiperspirant actives are listed in the Federal Register issued Aug. 20, 1982 pages 36492–36505. The title is; "Antiperspirant Drug Products for over the counter Human Use, Tentative Final Monograph".

2. A silicone wax conforming to the following structure

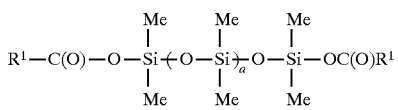

Wherein;

a is an integer ranging from 50–200;

$R^1$ is $C_{27}$–$C_{35}$.

The silicone wax is a key element in the preparation of the desired stick formula. Sticks made incorporating this essential ingredient remain uniform, have a smooth feel when applied to the skin and do not have any crystallization upon aging.

3. Cyclomethicone

The compositions of the present invention also contain cyclic silicones have the formula:

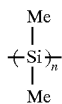

wherein:

Me is methyl;

n is an integer ranging from 3 to 9.

4. Another ingredient in the composition is a fatty alcohol conforming to the following structure:

$$CH_3\text{—}(CH_2)_s\text{—}OH$$

Wherein s is an integer ranging from 15 and 19.

DETAILED DESCRIPTION OF THE INVENTION

Specifically, the antiperspirant compositions of the current invention comprise:

1. Between 10 and 30% by weight of an antiperspirant active selected from the group consisting of aluminum chlorohydride, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesqichlorohydrex polyethylene glycol complex, aluminum zirconium trichlorohydrate, aluminum zirconium tetrachlorohydrate, aluminum zirconium pentachlorohydrate, aluminum zirconium octachlorohydrate, aluminum zirconium triclorohydrex glycerin complex, aluminum zirconium pentachlorohydrex glycerin complex, aluminum zirconium octachlorohydrex glycerin complex, aluminum chloride and aluminum sulfate buffered.

2. Between 1 and 20% by weight of a silicone wax conforming to the following structure:

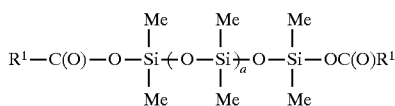

Wherein;

a is an integer ranging from 50–200;

$R^1$ is $C_{27}$–$C_{35}$.

The silicone wax is a key element in the preparation of the desired stick formula. Sticks made incorporating this essential ingredient remain uniform, have a smooth feel when applied to the skin and do not have any crystallization upon aging.

3. Between 35 and 55% by weight cyclomethicone having the formula:

wherein:

Me is methyl;

n is an integer ranging from 3 to 9.

and

4. Between 15 and 25% by weight of a fatty alcohol conforming to the following structure:

$$CH_3\text{—}(CH_2)_s\text{—}OH$$

Wherein s is an integer ranging from 15 and 19.

Preferred Embodiments

In a preferred embodiment, the antiperspirant composition of the present invention comprises;

1. Between 15 and 25% by weight of an antiperspirant active selected from the group consisting of aluminum chlorohydride, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesqichlorohydrex polyethylene glycol complex, aluminum zirconium trichlorohydrate, aluminum zirconium tetrachlorohydrate, aluminum zirconium pentachlorohydrate, aluminum zirconium octachlorohydrate, aluminum zirconium triclorohydrex glycerin complex, aluminum zirconium pentachlorohydrex glycerin complex, aluminum zirconium octachlorohydrex glycerin complex, aluminum chloride and aluminum sulfate buffered.

2. Between 5 and 20% by weight of a silicone wax conforming to the following structure

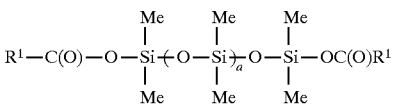

Wherein;

a is an integer ranging from 50–200;

$R^1$ is $C_{27}$–$C_{35}$.

The silicone wax is a key element in the preparation of the desired stick formula. Sticks made incorporating this essential ingredient remain uniform, have a smooth feel when applied to the skin and do not have any crystallization upon aging.

3. Between 30 and 50% by weight cyclomethicone having the formula:

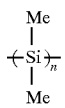

wherein:

Me is methyl;

n is an integer ranging from 3 to 9.

and

4. Between 10 and 25% by weight of a fatty alcohol conforming to the following structure:

$$CH_3-(CH_2)_s-OH$$

Wherein s is an integer ranging from 15 and 19.

In another preferred embodiment said antiperspirant active is aluminum chlorohydrate.

In another preferred embodiment the antiperspirant active is aluminum zircomium tetrachlorohydrate.

In another preferred embodiment the fatty alcohol has 18 carbons.

In another preferred embodiment said cyclic silicone has an n value of 4.

In a preferred embodiment said silicone wax has an "a" value of 150.

EXAMPLES

1. ANTIPERSPIRANT ACTIVES

Antiperspirant compounds useful in the practice of the present invention are commercially available from a number of manufacturers most importantly Rheis Corporation. Some examples are:

| Example | Material |
|---|---|
| 1. | aluminum chlorohydride, |
| 2. | aluminum dichlorohydrate, |
| 3. | aluminum sesquichlorohydrate, |
| 4. | aluminum chlorohydrex propylene glycol complex, |
| 5. | aluminum dichlorohydrex propylene glycol complex, |
| 6. | aluminum sesquichlorohydrex propylene glycol complex, |
| 7. | aluminum chlorohydrex polyethylene glycol complex, |
| 8. | aluminum dichlorohydrex polyethylene glycol complex, |
| 9. | aluminum sesqichlorohydrex polyethylene glycol complex, |
| 10. | aluminum zirconium trichlorohydrate, |
| 11. | aluminum zirconium tetrachlorohydrate, |
| 12. | aluminum zirconium pentachlorohydrate, |
| 13. | aluminum zirconium octachlorohydrate, |
| 14. | aluminum zirconium trichlorohydrex glycerin complex, |
| 15. | aluminum zirconium pentachlorohydrex glycerin complex, |
| 16. | aluminum zirconium octachlorohydrex glycerin complex, |
| 17. | aluminum chloride and aluminum sulfate buffered. |

2. SILICONE WAX

Silicone waxes of the type useful in the preparation of the compounds of the present invention are available from J.W. Hanson Inc. of Woodbury, N.Y.

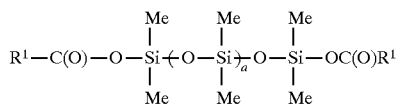

Wherein;

a is an integer ranging from 50–200;

$R^1$ is $C_{27}-C_{35}$.

| Example | a |
|---|---|
| 18 | 50 |
| 19 | 100 |
| 20 | 150 |
| 21 | 200 |

3. CYCLOMETHICONE

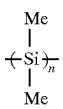

Cyclomethicone is an item of commerce available from a variety of sources including Dow Corning of Midland, Mich.

| Example | n |
|---|---|
| 22 | 3 |
| 23 | 4 |
| 24 | 5 |
| 25 | 9 |

4. FATTY ALCOHOL

Fatty alcohols are items of commerce. They are available from a variety of sources, most importantly, Henkel Corporation, Ambler, Pa.

| Example | s |
|---|---|
| 26 | 15 |
| 27 | 17 |
| 28 | 19 |

| Example | Active Ex./Gms | | Silicone Wax Example/ Grams | | Cyclomethicone Example/ Grams | | Fatty Alcohol Example/ Grams | |
|---|---|---|---|---|---|---|---|---|
| 29 | 1 | 10.0 | 18 | 20.0 | 22 | 40.0 | 26 | 25.0 |
| 30 | 2 | 15.0 | 19 | 15.0 | 23 | 45.0 | 27 | 25.0 |
| 31 | 3 | 20.0 | 20 | 10.0 | 24 | 55.0 | 28 | 10.0 |
| 32 | 4 | 25.0 | 21 | 5.0 | 25 | 45.0 | 26 | 25.0 |
| 33 | 5 | 30.0 | 18 | 1.0 | 22 | 45.0 | 27 | 10.0 |
| 34 | 6 | 25.0 | 19 | 15.0 | 23 | 55.0 | 28 | 25.0 |
| 35 | 7 | 20.0 | 20 | 15.0 | 24 | 40.0 | 26 | 25.0 |
| 36 | 8 | 20.0 | 21 | 15.0 | 25 | 45.0 | 27 | 10.0 |
| 37 | 9 | 15.0 | 18 | 20.0 | 22 | 55.0 | 28 | 10.0 |
| 38 | 10 | 18.0 | 19 | 2.0 | 23 | 37.0 | 26 | 10.0 |
| 39 | 11 | 10.0 | 20 | 15.0 | 24 | 47.0 | 27 | 25.0 |
| 40 | 12 | 20.0 | 21 | 20.0 | 25 | 50.0 | 28 | 12.0 |
| 41 | 13 | 30.0 | 18 | 15.0 | 22 | 55.0 | 26 | 10.0 |
| 42 | 14 | 27.0 | 19 | 1.0 | 23 | 45.0 | 27 | 20.0 |
| 43 | 15 | 25.0 | 20 | 18.0 | 24 | 45.0 | 28 | 12.0 |
| 44 | 16 | 20.0 | 21 | 20.0 | 25 | 50.0 | 26 | 10.0 |
| 45 | 17 | 20.0 | 18 | 20.0 | 25 | 35.0 | 27 | 25.0 |

Procedure:

The compositions of the present invention are prepared by heating the mixture of the components in a suitable vessel until homogeneous. The resulting homogeneous mixture is cast into forms to make sticks. Sticks made using the composition of the present invention are well suited for use in personal care applications.

We claim:

1. An antiperspirant compositions which comprises:
  1. Between 10 and 30% by weight of an antiperspirant active selected from the group consisting of aluminum chlorohydride, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesqichlorohydrex polyethylene glycol complex, aluminum zirconium trichlorohydrate, aluminum zirconium tetrachlorohydrate, aluminum zirconium pentachlorohydrate, aluminum zirconium octachlorohydrate, aluminum zirconium triclorohydrex glycerin complex, aluminum zirconium pentachlorohydrex glycerin complex, aluminum zirconium octachlorohydrex glycerin complex, aluminum chloride and aluminum sulfate buffered;

2. Between 1 and 20% by weight of a silicone wax conforming to the following structure:

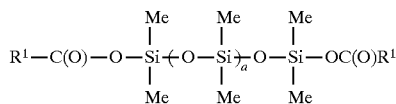

wherein;
a is an integer ranging from 50–200;
$R^1$ is $C_{27}$–$C_{35}$;

3. Between 35 and 55% by weight cyclomethicone having the formula:

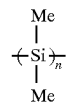

wherein:
Me is methyl;
n is an integer ranging from 3 to 9;

and

4. Between 15 and 25% by weight of a fatty alcohol conforming to the following structure:

Wherein s is an integer ranging from 15 and 19.

2. An antiperspirant composition of claim 1 wherein said active ranges in concentration between 15% and 25% by weight.

3. An antiperspirant composition of claim 1 wherein said silicone wax ranges in concentration between 5 and 20% by weight.

4. An antiperspirant composition of claim 1 wherein said cyclomethicone ranges in concentration from between 30% and 50% by weight.

5. An antiperspirant composition of claim 1 wherein said fatty alcohol ranges in concentration between 10 and 25% by weight.

6. An antiperspirant composition of claim 1 wherein said antiperspirant active is aluminum chlorohydrate.

7. An antiperspirant composition of claim 1 wherein said antiperspirant active is aluminum zircomium tetrachlorohydrate.

8. An antiperspirant composition of claim 1 s is 17.

9. An antiperspirant composition of claim 1 wherein n is 4.

10. An antiperspirant composition of claim 1 wherein a is 150.

* * * * *